United States Patent [19]
Bennett et al.

[11] Patent Number: 6,165,788
[45] Date of Patent: *Dec. 26, 2000

[54] ANTISENSE MODULATION OF SURVIVIN EXPRESSION

[75] Inventors: C. Frank Bennett, Carlsbad; Elizabeth J. Ackermann, Solana Beach; Eric E. Swayze; Lex M. Cowsert, both of Carlsbad, all of Calif.

[73] Assignee: Isis Pharmaceuticals, Inc., Carlsbad, Calif.

[ * ] Notice: This patent is subject to a terminal disclaimer.

[21] Appl. No.: 09/286,407

[22] Filed: Apr. 5, 1999

Related U.S. Application Data

[63] Continuation-in-part of application No. 09/163,162, Sep. 29, 1998.

[51] Int. Cl.[7] .......................... C07H 21/04; C07H 21/02; C12Q 1/68
[52] U.S. Cl. .............................. 435/375; 435/6; 435/377; 435/455; 536/23.1; 536/24.1; 536/24.5
[58] Field of Search .............................. 435/6, 375, 377, 435/455; 536/23.1, 24.1, 24.5; 514/44

[56] References Cited

FOREIGN PATENT DOCUMENTS

WO 98/22589  5/1998  WIPO .

OTHER PUBLICATIONS

Branch, A. "A Good Antisense Molecule is Hard to Find" TIBS vol. 23:45–50, Feb. 1998.

Agrawal, S. "Antisense oligonucleotides: Towards Clinical Trials" TIBTECH vol. 14:376–387, Oct. 1996.

Milner et al. "Selecting Effective Antisense Reagents on Combinitorial Arrays" Nature Biotechnology vol. 14: 537–541, Jun. 1997.

Li F., et al., "Control of apoptosis and mitotic spindle checkpoint by survivin", Nature, 1998, 386: 580–584.

*Primary Examiner*—John S. Brusca
*Assistant Examiner*—Sean Mc Garry
*Attorney, Agent, or Firm*—Law Offices of Jane Massey Licata

[57] ABSTRACT

Antisense compounds, compositions and methods are provided for modulating the expression of Survivin. The compositions comprise antisense compounds, particularly antisense oligonucleotides, targeted to nucleic acids encoding Survivin. Methods of using these compounds for modulation of Survivin expression and for treatment of diseases associated with expression of Survivin are provided.

2 Claims, No Drawings

ANTISENSE MODULATION OF SURVIVIN EXPRESSION

FIELD OF THE INVENTION

This application is a continuation-in-part of U.S. Ser. No. 09/163,162 filed Sep. 29, 1998.

The present invention provides compositions and methods for modulating the expression of Survivin. In particular, this invention relates to antisense compounds, particularly oligonucleotides, specifically hybridizable with nucleic acids encoding human Survivin. Such oligonucleotides have been shown to modulate the expression of Survivin.

BACKGROUND OF THE INVENTION

A hallmark feature of cancerous cells is uncontrolled proliferation. Among the differences that have been discovered between tumor and normal cells is resistance to the process of programmed cell death, also known as apoptosis (Ambrosini et al., Nat. Med., 1997, 3, 917–921). Apoptosis is a process multicellular organisms have evolved to prevent uncontrolled cell proliferation as well as to eliminate cells that have become sick, deleterious, or are no longer necessary. The process of apoptosis involves a multistep cascade in which cells are degraded from within through the concerted action of proteolytic enzymes and DNA endonucleases, resulting in the formation of apoptotic bodies that are then removed by scavenger cells. Research to date has shown that much of the intracellular degradation is carried out through the action of the caspases, a family of proteolytic enzymes that cleave adjacent to aspartate residues (Cohen, Biochemistry Journal, 1997, 326, 1–16).

The finding that most tumor cells display resistance to the apoptotic process has led to the view that therapeutic strategies aimed at attenuating the resistance of tumor cells to apoptosis could represent a novel means to halt the spread of neoplastic cells (Ambrosini et al., Nat. Med., 1997, 3, 917–921). One of the mechanisms through which tumor cells are believed to acquire resistance to apoptosis is by overexpression of Survivin, a recently described member of the IAP (inhibitor of apoptosis) caspase inhibitor family. To date, overexpression of Survivin has been detected in tumors of the lung, colon, pancreas, prostate, breast, stomach, non-Hodgkin's lymphoma, and neuroblastoma (Adida et al., Lancet, 1998, 351, 882–883; Ambrosini et al., Nat. Med., 1997, 3, 917–921; Lu et al., Cancer Res., 1998, 58, 1808–1812). A more detailed analysis has been performed in neuroblastoma where it was found that Survivin overexpression segregated with tumor histologies known to associate with poor prognosis (Adida et al., Lancet, 1998, 351, 882–883). Finally, Ambrosini et al. describe transfection of HeLa cells with an expression vector containing a 708 nt fragment of the human cDNA encoding effector cell protease receptor 1 (EPR-1), the coding sequence of which is extensively complementary to the coding strand of Survivin (Ambrosini et al., J. Bio. Chem., 1998, 273, 11177–11182) and which potentially acts as a Survivin antisense RNA. This construct caused a reduction in cell viability. Methods for modulating apoptosis and for reducing the severity of a pathological state mediated by Survivin using agents that modulate amounts or activity of Survivin are disclosed in WO 98/22589, which also discloses the EPR-1 coding strand/Survivin antisense construct described by Ambrosini et al., supra.

Survivin has recently been found to play a role in cell cycle regulation. It has been found to be expressed in the G2/M phase of the cell cycle in a cycle-regulated manner, and associates with microtubules of the mitotic spindle. Disruption of this interaction results in loss of Survivin's anti-apoptotic function and increased caspase-3 activity during mitosis. Caspase-3 is associated with apoptotic cell death. It is therefore believed that Survivin may counteract a default induction of apoptosis in G2/M phase. It is believed that the overexpression of Survivin in cancer may overcome this apoptotic checkpoint, allowing undesired survival and division of cancerous cells. The Survivin antisense construct described by Ambrosini above was found to downregulate endogenous Survivin in HeLa cells and to increase caspase-3-dependent apoptosis in cells in G2/M phase. Li et al., Nature, 1998, 396, 580–584.

As a result of these advances in the understanding of apoptosis and the role that Survivin expression is believed to play in conferring a growth advantage to a wide variety of tumor cell types, there is a great desire to provide compositions of matter which can modulate the expression of Survivin. It is greatly desired to provide methods of diagnosis and detection of nucleic acids encoding Survivin in animals. It is also desired to provide methods of diagnosis and treatment of conditions arising from Survivin expression. In addition, improved research kits and reagents for detection and study of nucleic acids encoding Survivin are desired.

Currently, there are no known therapeutic agents which effectively inhibit the synthesis of Survivin. Consequently, there is a long-felt need for agents capable of effectively inhibiting Survivin expression in tumor cells. Antisense oligonucleotides against Survivin may therefore prove to be uniquely useful in a number of therapeutic, diagnostic and research applications.

SUMMARY OF THE INVENTION

The present invention is directed to antisense compounds, particularly oligonucleotides, which are targeted to a nucleic acid encoding Survivin, and which modulate the expression of Survivin. Pharmaceutical and other compositions comprising the antisense compounds of the invention are also provided. Further provided are methods of modulating the expression of Survivin in cells or tissues comprising contacting said cells or tissues with one or more of the antisense compounds or compositions of the invention. Further provided are methods of treating an animal, particularly a human, suspected of having or being prone to a disease or condition associated with expression of Survivin by administering a therapeutically or prophylactically effective amount of one or more of the antisense compounds or compositions of the invention.

DETAILED DESCRIPTION OF THE INVENTION

The present invention employs oligomeric antisense compounds, particularly oligonucleotides, for use in modulating the function of nucleic acid molecules encoding Survivin, ultimately modulating the amount of Survivin produced. This is accomplished by providing antisense compounds which specifically hybridize with one or more nucleic acids encoding Survivin. As used herein, the terms "target nucleic acid" and "nucleic acid encoding Survivin" encompass DNA encoding Survivin, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of Survivin. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding Survivin. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding Survivin, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, or in the case of in vitro assays, under conditions in which the assays are performed.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases. Particularly preferred are antisense oligonucleotides comprising from about 8 to about 30 nucleobases (i.e. from about 8 to about 30 linked nucleosides). Preferred embodiments comprise at least an 8-nucleobase portion of a sequence of an antisense compound which inhibits expression of Survivin. As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science,* 1991, 254, 1497–1500.

Most preferred embodiments of the invention are oligonucleotides with phosphorothioate backbones and oligonucleosides with heteroatom backbones, and in particular —CH$_2$—NH—O—CH$_2$—, —CH$_2$—N(CH$_3$)—O—CH$_2$— [known as a methylene (methylimino) or MMI backbone], —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— [wherein the native phosphodiester backbone is represented as —O—P—O—CH$_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. Particularly preferred are O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10. Other preferred oligonucleotides comprise one of the following at the 2' position: C$_1$ to C$_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O-CH$_2$CH$_2$OCH$_3$, also known as 2'-O-(2-methoxyethyl) or 2'-MOE) (Martin et al., *Helv. Chim. Acta,* 1995, 78, 486–504) i.e., an alkoxyalkoxy group. A further preferred modification includes 2'-dimethylaminooxyethoxy, i.e., a O(CH$_2$)$_2$ON(CH$_3$)$_2$ group, also known as 2'-DMAOE, as described in U.S. patent application Ser. No. 09/016,520, filed on Jan. 30, 1998, which is commonly owned with the instant application and the contents of which are herein incorporated by reference.

Other preferred modifications include 2'-methoxy (2'-O-CH$_3$), 2'-aminopropoxy (2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in *The Concise Encyclopedia Of Polymer Science And Engineering,* pages 858–859, Kroschwitz, J. I., ed. John Wiley & Sons, 1990, those disclosed by Englisch et al., *Angewandte Chemie,* International Edition, 1991, 30, 613, and those disclosed by Sanghvi, Y. S., Chapter 15, *Antisense Research and Applications,* pages 289–302, Crooke, S. T. and Lebleu, B. , ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyl-adenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications,* CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,750,692, each of which is herein incorporated by reference.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA,* 1989, 86, 6553–6556), cholic acid (Manoharan et al., *Bioorg. Med. Chem. Let.,* 1994, 4, 1053–1060), a thioether, e.g., hexyl-S-tritylthiol (Manoharan et al.,*Ann. N.Y. Acad. Sci.,* 1992, 660, 306–309; Manoharan et al., Bioorg. Med. Chem. Let., 1993, 3, 2765–2770), a thiocholesterol (Oberhauser et al., *Nucl. Acids Res.,* 1992, 20, 533–538), an aliphatic chain, e.g., dodecandiol or undecyl residues (Saison-Behmoaras et al., *EMBO J.,* 1991, 10, 1111–1118; Kabanov et al., *FEBS Lett.,* 1990, 259, 327–330; Svinarchuk et al., *Biochimie,* 1993, 75, 49–54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651–3654; Shea et al., *Nucl. Acids Res.,* 1990, 18, 3777–3783), a polyamine or a polyethylene glycol chain (Manoharan et al., *Nucleosides & Nucleotides,* 1995, 14, 969–973), or adamantane acetic acid (Manoharan et al., *Tetrahedron Lett.,* 1995, 36, 3651–3654), a palmityl moiety (Mishra et al., *Biochim. Biophys. Acta,* 1995, 1264, 229–237), or an octadecylamine or hexylamino-carbonyl-oxycholesterol moiety (Crooke et al., *J. Pharmacol. Exp. Ther.,* 1996, 277, 923–937.

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717; 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459, 127; 5,521,291; 5,543,158; 5,547,932; 5,583,020; 5,591, 721; 4,426,330; 4,534,899; 5,013,556; 5,108,921; 5,213, 804; 5,227,170; 5,264,221; 5,356,633; 5,395,619; 5,416, 016; 5,417,978; 5,462,854; 5,469,854; 5,512,295; 5,527, 528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.,* 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfoic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine. The antisense compounds of the present invention can be utilized for diagnostics, therapeutics, prophylaxis and as research reagents and kits. For therapeutics, an animal, preferably a human, suspected of having a disease or disorder which can be treated by modulating the expression of Survivin is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding Survivin, enabling sandwich and other assays to easily be constructed to exploit this fact. Hybridization of the antisense oligonucleotides of the invention with a nucleic acid encoding Survivin can be detected by means known in the art. Such means may include conjugation of an enzyme to the oligonucleotide, radiolabelling of the oligonucleotide or any other suitable detection means. Kits using such detection means for detecting the level of Survivin in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions and/or formulations comprising the oligonucleotides of the present invention may also include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., *Critical Reviews in Therapeutic Drug Carrier Systems*, 1991, 8, 91–192; Muranishi, *Critical Reviews in Therapeutic Drug Carrier Systems*, 1990, 7:1, 1–33). One or more penetration enhancers from one or more of these broad categories may be included.

Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arichidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., *Critical Reviews in Therapeutic Drug Carrier Systems,* 1991, 8:2, 91–192; Muranishi, *Critical Reviews in Therapeutic Drug Carrier Systems,* 1990, 7:1, 1–33; El-Hariri et al., *J. Pharm. Pharmacol.,* 1992, 44, 651–654). Examples of some presently preferred fatty acids are sodium caprate and sodium laurate, used singly or in combination at concentrations of 0.5 to 5%.

The physiological roles of bile include the facilitation of dispersion and absorption of lipids and fat-soluble vitamins (Brunton, Chapter 38 In: *Goodman & Gilman's The Pharmacological Basis of Therapeutics,* 9th Ed., Hardman et al., eds., McGraw-Hill, New York, N.Y., 1996, pages 934–935). Various natural bile salts, and their synthetic derivatives, act as penetration enhancers. Thus, the term "bile salt" includes any of the naturally occurring components of bile as well as any of their synthetic derivatives. Examples of presently preferred bile salts are chenodeoxycholic acid (CDCA) and/or ursodeoxycholic acid (UDCA), generally used at concentrations of 0.5 to 2%.

Complex formulations comprising one or more penetration enhancers may be used. For example, bile salts may be used in combination with fatty acids to make complex formulations. Preferred combinations include CDCA combined with sodium caprate or sodium laurate (generally 0.5 to 5%).

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems,* 1991, 8:2, 92–192; Muranishi, *Critical Reviews in Therapeutic Drug Carrier Systems,* 1990, 7:1, 1–33; Buur et al., *J. Control Rel.,* 1990, 14, 43–51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., *Critical Reviews in Therapeutic Drug Carrier Systems,* 1991, 8:2, 92–191); and perfluorochemical emulsions, such as FC-43 (Takahashi et al., *J. Pharm. Pharmacol.,* 1988, 40, 252–257).

Non-surfactants include, for example, unsaturated cyclic ureas, 1-alkyl- and 1-alkenylazacyclo-alkanone derivatives (Lee et al., *Critical Reviews in Therapeutic Drug Carrier Systems,* 1991, 8:2, 92–191); and non-steroidal anti-inflammatory agents such as diclofenac sodium, indomethacin and phenylbutazone (Yamashita et al., *J. Pharm. Pharmacol.,* 1987, 39, 621–626).

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioated oligonucleotide in hepatic tissue is reduced when it is coadministered with polyinosinic acid, dextran sulfate, polycytidic acid or 4-acetamido-4'-isothiocyano-stilbene-2,2'-disulfonic acid (Miyao et al., *Antisense Res. Dev.,* 1995, 5, 115–121; Takakura et al., *Antisense & Nucl. Acid Drug Dev.,* 1996, 6, 177–183).

In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinyl-pyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the antisense compounds of the invention are introduced into a patient, colloidal dispersion systems may be used as delivery vehicles to enhance the in vivo stability of the compounds and/or to target the compounds to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layer(s) made up of lipids arranged in a bilayer configuration (see, generally, Chonn et al., *Current Op. Biotech.,* 1995, 6, 698–708).

Certain embodiments of the invention provide for liposomes and other compositions containing (a) one or more antisense compounds and (b) one or more other chemotherapeutic agents which function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). See, generally, *The Merck Manual of Diagnosis and Therapy*, 15th Ed., Berkow et al., eds., 1987, Rahway, N.J., pages 1206–1228). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Examples of antisense oligonucleotides include, but are not limited to, those directed to the following targets as disclosed in the indicated U.S. Patents, or pending U.S. applications, which are commonly owned with the instant application and are hereby incorporated by reference, or the indicated published PCT applications: raf (WO 96/39415, WO 95/32987 and U.S. Pat. Nos. 5,563,255 and 5,656,612), the p120 nucleolar antigen (WO 93/17125 and U.S. Pat. No. 5,656,743), protein kinase C (WO 95/02069, WO 95/03833 and WO 93/19203), multi-drug resistance-associated protein (WO 95/10938 and U.S. Pat. No. 5,510,239), subunits of transcription factor AP-1 (pending application U.S. Ser. No. 08/837,201, filed Apr. 14, 1997), Jun kinases (pending application U.S. Ser. No. 08/910,629, filed Aug. 13, 1997), MDR-1 (multidrug resistance glycoprotein; pending application U.S. Ser. No. 08/731,199, filed Sep. 30, 1997), HIV (U.S. Pat. Nos. 5,166,195 and 5,591,600), herpesvirus (U.S. Pat. Nos. 5,248,670 and 5,514,577), cytomegalovirus (U.S. Pat. Nos. 5,442,049 and 5,591,720), papillomavirus (U.S. Pat. No. 5,457,189), intercellular adhesion molecule-1 (ICAM-1) (U.S. Pat. No. 5,514,788), 5-lipoxygenase (U.S. Pat. No. 5,530,114) and influenza virus (U.S. Pat. No. 5,580,767). Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy Amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research*, 1993, 21, 3197–3203] using commercially available phosphoramidites (Glen Research, Sterling Va. or ChemGenes, Needham Mass.).

2'-Fluoro Amidites

2'-Fluorodeoxyadenosine Amidites

2'-fluoro oligonucleotides were synthesized as described previously [Kawasaki, et. al., *J. Med. Chem.*, 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) Modified Amidites

2'-O-Methoxyethyl-substituted nucleoside amidites are prepared as follows, or alternatively, as per the methods of Martin, P., *Helvetica Chimica Acta*, 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/Acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 hours using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in $CHCl_3$ (700 mL) and extracted with saturated $NaHCO_3$, (2×300 mL) and saturated NaCl (2×300 mL), dried over $MgSO_4$ and evaporated to give a residue (96 g). The residue was chromatographed on a 1.5 kg silica column using EtOAc/Hexane (1:1) containing 0.5% $Et_3NH$ as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in $CH_2Cl_2$ (1 L). Tetrazole diisopropylamine (7.1 g) and 2-cyanoethoxy-tetra- (isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc/Hexane (3:1) as the eluting solvent. The pure fractions were combined to give 90.6 g (87%) of the title compound.

2'-(Aminooxyethyl) nucleoside amidites and 2'-(dimethylaminooxyethyl) nucleoside amidites Aminooxyethyl and dimethylaminooxyethyl amidites are prepared as per the methods of U.S. Patent Applications Ser. No. 10/037,143, filed Feb. 14, 1998, and Ser. No. 09/016, 520, filed Jan. 30, 1998, each of which is commonly owned with the instant application and is herein incorporated by reference.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 hours), the oligonucleotides were purified by precipitating twice with 2.5 volumes of ethanol from a 0.5 M NaCl solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625, 050, herein incorporated by reference.

Phosphoramidite oligonucleotides are prepared as described in U.S. Pat. Nos., 5,256,775 or 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethyl-hydrazo linked oligonucleosides, also identified as MDH linked oligonucleosides, and methylenecarbonylamino linked oligonucleosides, also identified as amide-3 linked oligonucleosides, and methyleneaminocarbonyl linked oligo-nucleosides, also identified as amide-4 linked oligonucleo-sides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] chimeric phosphorothioate oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 Ammonia/Ethanol at room temperature overnight then lyophilized to dryness. Treatment in methanolic ammonia for 24 hours at room temperature is then done to deprotect all bases and sample was again lyophilized to dryness. The pellet is resuspended in 1M TBAF in THF for 24 hours at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]-[2'-deoxy]-[2'-O-(Methoxyethyl)] chimeric phosphorothioate oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl) Phosphodiester]-[2'-deoxy Phosphorothioate]-[2'-O-(2-Methoxyethyl) Phosphodiester] chimeric oligonucleotides

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6
Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7
Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif. or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8
Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9
Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following four cell types are provided for illustrative purposes, but other cell types can be routinely used.

T-24 Cells

The transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF Cells

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK cells

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

Treatment with antisense compounds

When cells reached 80% confluency, they were treated with oligonucleotide. For cells grown in 96-well plates, wells were washed once with 200 µL OPTI-MEM™-1 reduced-serum medium (Gibco BRL) and then treated with 130 µL of OPTI-MEM™-1 containing 3.75 µg/mL LIPO-FECTIN™ (Gibco BRL) and the desired oligonucleotide at a final concentration of 150 nM. After 4 hours of treatment, the medium was replaced with fresh medium. Cells were harvested 16 hours after oligonucleotide treatment.

Example 10

Analysis of Oligonucleotide Inhibition of Survivin Expression

Antisense modulation of Survivin expression can be assayed in a variety of ways known in the art. For example, Survivin mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. Methods of RNA isolation are taught in, for example, Ausubel, F. M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions. Other methods of PCR are also known in the art.

Survivin protein levels can be quantitated in a variety of ways well known in the art, such as immunoprecipitation, Western blot analysis (immunoblotting), ELISA or fluorescence-activated cell sorting (FACS). Antibodies directed to Survivin can be identified and obtained from a variety of sources, such as the MSRS catalog of antibodies (Aerie Corporation, Birmingham, Minn.), or can be prepared via conventional antibody generation methods. Methods for preparation of polyclonal antisera are taught in, for example, Ausubel, F. M. et al., *Current Protocols in Molecular Biology*, Volume 2, pp. 11.12.1–11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1–11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1–10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1–11.2.22, John Wiley & Sons, Inc., 1991.

Example 11

Poly(A)+ mRNA Isolation

Poly(A)+ mRNA was isolated according to Miura et al., *Clin. Chem.*, 1996, 42, 1758–1764. Other methods for poly(A)+ mRNA isolation are taught in, for example, Ausubel, F. M. et al., *Current Protocols in Molecular Biology*, Volume 1, pp. 4.5.1–4.5.3, John Wiley & Sons, Inc., 1993. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total mRNA was isolated using an RNEASY 96™ kit and buffers purchased from Qiagen Inc. (Valencia Calif.) following the manufacturer's recommended procedures. Briefly, for cells grown on 96-well plates, growth medium was removed from the cells and each well was washed with 200 µL cold PBS. 100 µL Buffer RLT was added to each well and the plate vigorously agitated for 20 seconds. 100 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 µL water into each well, incubating 1 minute, and then applying the vacuum for 30 seconds. The elution step was repeated with an additional 60 µL water.

Example 13

Real-time Quantitative PCR Analysis of Survivin mRNA Levels

Quantitation of Survivin mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE or FAM, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular (six-second) intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

PCR reagents were obtained from PE-Applied Biosystems, Foster City, Calif. RT-PCR reactions were carried out by adding 25 μL PCR cocktail (1× TAQMAN™ buffer A, 5.5 mM MgCl$_2$, 300 μM each of dATP, dCTP and dGTP, 600 μM of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 μL poly(A) mRNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension). Survivin probes and primers were designed to hybridize to the human Survivin sequence, using published sequence information (GenBank accession number U75285, incorporated herein as SEQ ID NO:1).

For Survivin the PCR primers were: forward primer: AAGGACCACCGCATCTCTACA (SEQ ID NO: 2) reverse primer: CCAAGTCTGGCTCGTTCTCAGT (SEQ ID NO: 3) and the PCR probe was: FAM-CGAGGCTGGCTTCATCCACTGCC-TAMRA (SEQ ID NO: 4) where FAM (PE-Applied Biosystems, Foster City, Calif.) is the fluorescent reporter dye) and TAMRA (PE-Applied Biosystems, Foster City, Calif.) is the quencher dye.

For GAPDH the PCR primers were: forward primer: GAAGGTGAAGGTCGGAGTC (SEQ ID NO: 5) reverse primer: GAAGATGGTGATGGGATTTC (SEQ ID NO: 6) and the PCR probe was: 5' JOE-CAAGCTTCCCGTTCTCAGCC-TAMRA 3' (SEQ ID NO: 7) where JOE (PE-Applied Biosystems, Foster City, Calif.) is the fluorescent reporter dye) and TAMRA (PE-Applied Biosystems, Foster City, Calif.) is the quencher dye.

Example 14

Northern blot analysis of Survivin mRNA levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.).

Membranes were probed using QUICKHYB™ hybridization solution (Stratagene, La Jolla, Calif.) using manufacturer's recommendations for stringent conditions with a Survivin specific probe prepared by PCR using the forward primer AAGGACCACCGCATCTCTACA (SEQ ID NO: 2) and the reverse primer CCAAGTCTGGCTCGTTCTCAGT (SEQ ID NO: 3). To normalize for variations in loading and transfer efficiency membranes were stripped and probed for glyceraldehyde-3-phosphate dehydrogenase (GAPDH) RNA (Clontech, Palo Alto, Calif.). Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense inhibition of Survivin expression-phosphorothioate oligodeoxynucleotides In accordance with the present invention, a series of oligonucleotides were designed to target different regions of the human Survivin RNA, using published sequences (GenBank accession number U75285, incorporated herein as SEQ ID NO: 1). The oligonucleotides are shown in Table 1. Target sites are indicated by nucleotide numbers, as given in the sequence source reference (Genbank accession no. U75285), to which the oligonucleotide binds. All compounds in Table 1 are oligodeoxynucleotides with phosphorothioate backbones (internucleoside linkages) throughout. The compounds were analyzed for effect on Survivin mRNA levels by quantitative real-time PCR as described in other examples herein. Data are averages from three experiments. If present, "N.D." indicates "no data".

TABLE 1

Inhibition of Survivin mRNA levels by phosphorothioate oligodeoxynucleotides

| IRIS# | REGION | TARGET SITE | SEQUENCE | % Inhibition | SEQ ID NO. |
|---|---|---|---|---|---|
| 23652 | 5' UTR | 1 | gcgattcaaatctggcgg | 0 | 8 |
| 23653 | 5' UTR | 19 | cctctgccaacgggtccc | 4 | 9 |
| 23654 | 5' UTR | 75 | tgagaaagggctgccagg | 46 | 10 |
| 23655 | 5' UTR | 103 | ttcttgaatgtagagatg | 0 | 11 |
| 23656 | 5' UTR | 128 | ggcgcagccctccaagaa | 38 | 12 |
| 23657 | Coding | 194 | caagtctggctcgttctc | 0 | 13 |
| 23658 | Coding | 226 | tccagctccttgaagcag | 32 | 14 |
| 23659 | Coding | 249 | ggtcgtcatctggctccc | 36 | 15 |
| 23660 | Coding | 306 | gcttcttgacagaaagga | 35 | 16 |
| 23661 | Coding | 323 | ggttaattcttcaaactg | 0 | 17 |
| 23662 | Coding | 363 | tcttggctctttctctgt | 34 | 18 |
| 23663 | Coding | 393 | tcttattgttggtttcct | 0 | 19 |
| 23664 | Coding | 417 | tcgcagtttcctcaaatt | 37 | 20 |
| 23665 | Coding | 438 | cgatggcacggcgcactt | 72 | 21 |
| 23666 | Coding | 511 | cctggaagtggtgcagcc | 16 | 22 |
| 23667 | Coding | 542 | acaggaaggctggtggca | 70 | 23 |
| 23668 | Coding | 587 | tttgaaaatgttgatctc | 8 | 24 |
| 23669 | Coding | 604 | acagttgaaacatctaat | 0 | 25 |
| 23670 | Coding | 625 | ctttcaagacaaaacagg | 0 | 26 |
| 23671 | Coding | 650 | acaggcagaagcacctct | 0 | 27 |
| 23672 | Coding | 682 | aagcagccactgttacca | 64 | 28 |
| 23673 | Coding | 700 | aaagagagagagagagag | 18 | 29 |
| 23674 | Coding | 758 | tccctcacttctcacctg | 29 | 30 |
| 23675 | 3' UTR | 777 | agggacactgccttcttc | 43 | 31 |
| 23676 | 3' UTR | 808 | ccacgcgaacaaagctgt | 62 | 32 |
| 23677 | 3' UTR | 825 | actgtggaaggctctgcc | 0 | 33 |
| 23678 | 3' UTR | 867 | aggactgtgacagcctca | 62 | 34 |
| 23679 | 3' UTR | 901 | tcagattcaacaggcacc | 0 | 35 |
| 23680 | 3' UTR | 1016 | attctctcatcacacaca | 26 | 36 |
| 23681 | 3' UTR | 1054 | tgttgttaaacagtagag | 0 | 37 |
| 23682 | 3' UTR | 1099 | tgtgctattctgtgaatt | 20 | 38 |
| 23683 | 3' UTR | 1137 | gacttagaatggctttgt | 37 | 39 |
| 23684 | 3' UTR | 1178 | ctgtctcctcatccacct | 41 | 40 |
| 23685 | 3' UTR | 1216 | aaaaggagtatctgccag | 39 | 41 |
| 23686 | 3' UTR | 1276 | gaggagcggccagcatgt | 47 | 42 |
| 23687 | 3' UTR | 1373 | ggctgacagacacacggc | 41 | 43 |
| 23688 | 3' UTR | 1405 | ccgtgtggagaacgtgac | 22 | 44 |
| 23689 | 3' UTR | 1479 | tacgccagagttcagccc | 1 | 45 |
| 23690 | 3' UTR | 1514 | atgacagggaggagggcg | 0 | 46 |
| 23691 | 3' UTR | 1571 | gccgagatgacctccaga | 66 | 47 |

As shown in Table 1, SEQ ID NOs 10, 12, 14, 15, 16, 18, 20, 21, 23, 28, 31, 32, 34, 39, 40, 41, 42, 43 and 47 demonstrated at least 30% inhibition of Survivin expression in this assay and are therefore preferred.

Example 16

Antisense inhibition of Survivin expression-phosphorothioate 2'-MOE gapmer oligonucleotides In accordance with the present invention, a second series of oligonucleotides targeted to human Survivin were synthesized. The oligonucleotide sequences are shown in Table 2. Target sites are indicated by nucleotide numbers, as given in the sequence source reference (Genbank accession no. U75285), to which the oligonucleotide binds.

All compounds in Table 2 are chimeric oligonucleotides ("gapmers") 18 nucleotides in length, composed of a central "gap" region consisting of ten 2'-deoxynucleotides, which is flanked on both sides (5' and 3' directions) by four-nucleotide "wings". The wings are composed of 2'-methoxyethyl (2'-MOE)nucleotides. The internucleoside (backbone) linkages are phosphorothioate (P=S) throughout the oligonucleotide. Cytidine residues in the 2'-MOE wings are 5-methylcytidines.

Data were obtained by real-time quantitative PCR as described in other examples herein and are averaged from three experiments. If present, "N.D." indicates "no data".

TABLE 2

Inhibition of Survivin mRNA levels by chimeric phosphorothioate oligonucleotides having 2'-MOE wings and a deoxy gap

| IRIS# | REGION | TARGET SITE | SEQUENCE | % Inhibition | SEQ ID NO. |
|---|---|---|---|---|---|
| 23692 | 5' UTR | 1 | gcgattcaaatctggcgg | 22 | 8 |
| 23693 | 5' UTR | 19 | cctctgccaacgggtccc | 15 | 9 |
| 23694 | 5' UTR | 75 | tgagaaagggctgccagg | 11 | 10 |
| 23695 | 5' UTR | 103 | ttcttgaatgtagagatg | 37 | 11 |
| 23696 | 5' UTR | 128 | ggcgcagccctccaagaa | 16 | 12 |
| 23697 | Coding | 194 | caagtctggctcgttctc | 17 | 13 |
| 23698 | Coding | 226 | tccagctccttgaagcag | 0 | 14 |
| 23699 | Coding | 249 | ggtcgtcatctggctccc | 19 | 15 |
| 23700 | Coding | 306 | gcttcttgacagaaagga | 35 | 16 |
| 23701 | Coding | 323 | ggtttaattcttcaaactg | 15 | 17 |
| 23702 | Coding | 363 | tcttggctctttctctgt | 8 | 18 |
| 23703 | Coding | 393 | tcttattgttggtttcct | 41 | 19 |
| 23704 | Coding | 417 | tcgcagtttcctcaaatt | 24 | 20 |
| 23705 | Coding | 438 | cgatggpapggcgcactt | 72 | 21 |
| 23706 | Coding | 511 | cctggaagtggtgcagcc | 4 | 22 |
| 23707 | Coding | 542 | acaggaaggctggtggca | 48 | 23 |
| 23708 | Coding | 587 | tttgaaaatgttgatctc | 2 | 24 |
| 23709 | Coding | 604 | acagttgaaacatctaat | 28 | 25 |
| 23710 | Coding | 625 | ctttcaagacaaaacagg | c | 26 |
| 23711 | Coding | 650 | acaggcagaagcacctct | 38 | 27 |
| 23712 | Coding | 682 | aagcagccactgttacca | 27 | 28 |
| 23713 | Coding | 700 | aaagagagagagagagag | 0 | 29 |
| 23714 | Coding | 758 | tccctcacttctcacctg | c | 30 |
| 23715 | 3' UTR | 777 | agggacactgccttcttc | 44 | 31 |
| 23716 | 3' UTR | 808 | ccacgcgaacaaagctgt | 25 | 32 |
| 23717 | 3' UTR | 825 | actgtggaaggctctgcc | 8 | 33 |
| 23718 | 3' UTR | 867 | aggactgtgacagcctca | 49 | 34 |
| 23719 | 3' UTR | 901 | tcagattgaacaggcacc | 0 | 35 |
| 23720 | 3' UTR | 1016 | attctctcatcacacaca | 0 | 36 |
| 23721 | 3' UTR | 1054 | tgttgttaaacagtagag | 0 | 37 |
| 23722 | 3' UTR | 1099 | tgtgctattctgtgaatt | 80 | 38 |
| 23723 | 3' UTR | 1137 | gacttagaatggctttgt | 44 | 39 |
| 23724 | 3' UTR | 1178 | ctgtctcctcatccacct | 27 | 40 |
| 23725 | 3' UTR | 1216 | aaaaggagtatctgccag | 21 | 41 |
| 23726 | 3' UTR | 1276 | gaggagcggccagcatgt | 39 | 42 |
| 23727 | 3' UTR | 1373 | ggctgacagacacacggc | 45 | 43 |
| 23728 | 3' UTR | 1405 | ccgtgtggagaaogtgac | 24 | 44 |
| 23729 | 3' UTR | 1479 | tacgccagacttcagccc | 25 | 45 |
| 23730 | 3' UTR | 1514 | atgacagggaggagggcg | 0 | 46 |
| 23731 | 3' UTR | 1571 | gccgagatgacotccaga | 19 | 47 |

As shown in Table 2, SEQ ID NOs 11, 16, 19, 21, 23, 27, 31, 34, 38, 39, 42 and 43 demonstrated at least 30% inhibition of Survivin expression in this experiment and are therefore preferred.

Example 17
Western blot analysis of Survivin protein levels

Western blot analysis (immunoblot analysis) is carried out using standard methods. Cells are harvested 16–20 hours after oligonucleotide treatment, washed once with PBS, suspended in Laemmli buffer (100 μl/well), boiled for 5 minutes and loaded on a 16% SDS-PAGE gel. Gels are run for 1.5 hours at 150 V, and transferred to membrane for western blotting. Appropriate primary antibody directed to Survivin is used, with a radiolabelled or fluorescently labeled secondary antibody directed against the primary antibody species. Bands are visualized using a PHOSPHO-RIMAGER™ (Molecular Dynamics, Sunnyvale Calif.).

Example 18
Effect of Survivin antisense oligonucleotide on apoptosis

ISIS 23722 and a mismatch control, ISIS 28598 (TAAGCTGTTCTATGTGTT; SEQ ID NO: 48) were assayed for their effect on apoptosis in HeLa cells. The caspase inhibitor z-VAD.fmk was purchased from Calbiochem (La Jolla Calif.) and used according to manufacturer's recommendations. In HeLa cells without oligonucleotide, approximately 4% of cells are hypodiploid (indicating DNA fragmentation, a measure of apoptosis). With the addition of ISIS 23722, approximately 22% of cells are hypodiploid, compared to approximately 11% with the mismatch oligonucleotide. In the presence of the caspase inhibitor z-VAD.fmk (42.8 mM), the percent of hypodiploid (apoptotic) cells drops to 3% without oligonucleotide, 6% with ISIS 23722 and 4% with the mismatch control. This demonstrates that antisense inhibition of Survivin increases apoptosis and this effect is caspase-mediated.

Example 18
Effect of antisense inhibition of Survivin on cytokinesis

HeLa cells treated with an antisense oligonucleotide targeted to Survivin (ISIS 23722) can be observed to form large, multinucleated cells as a result of improper cell division. The mismatch control oligonucleotide did not have this effect and cells appeared normal (comparable to untreated controls). This effect can be quantitated by flow cytometry.

Untreated cells or cells treated with the control oligonucleotide display two prominent peaks, representing populations of cells in the G1 phase and the G2/M phase of cell division, respectively. G1 cells have a single copy of their DNA (1×) and G2/M cells have two copies (2×). Over time from 24 hours to 72 hours, these 1× and 2× peaks remain virtually unchanged in cells treated with the control oligonucleotide or without oligonucleotide. However, in cells treated with the antisense oligonucleotide targeted to Survivin, the majority of cells have two copies of DNA by 24 hours after oligo treatment. This indicates that cell division is arrested. By 48 hours after treatment with this oligonucleotide, a 4× peak is approximately equal in size to the 1× and 2× peaks, indicating roughly equal numbers of cells with one, two and four copies of DNA. By 72 hours the largest peak is 16×, indicating that cells have 16 copies of their DNA and thus that division of the cytoplasm has not occurred for multiple generations. Thus inhibition of Survivin is shown to interfere with cytokinesis.

What is claimed is:

1. A method of modulating cytokinesis in a cell *in vitro* comprising contacting said cell with an antisense compound 8 to 30 nucleobases in length targeted to a nucleic acid molecule encoding human Survivin and which inhibits the expression of human Survivin so that cytokinesis is modulated.

2. A method of modulating the cell cycle in a cell comprising contacting said cell *in vitro* with an antisense compound 8 to 30 nucleotides in length targeted to a nucleic acid molecule encoding human Survivin and which inhibits the expression of human Survivin so that the cell cycle is modulated.

\* \* \* \* \*

UNITED STATES PATENT AND TRADEMARK OFFICE
CERTIFICATE OF CORRECTION

PATENT NO. : 6,165,788
DATED : December 26, 2000
INVENTOR(S) : Bennett et al.

Page 1 of 1

It is certified that error appears in the above-identified patent and that said Letters Patent is hereby corrected as shown below:

<u>Column 24,</u>
Line 54, please delete "RWI" and insert -- RPE --.

<u>Column 29, Table 2,</u>
Column 5, row 24, please delete "c" and insert -- 0 --.
Column 5, row 28, please delete "c" and insert -- 0 --.

Signed and Sealed this

Twenty-ninth Day of January, 2002

Attest:

Attesting Officer

JAMES E. ROGAN
Director of the United States Patent and Trademark Office

SEQUENCE LISTING

```
<160> NUMBER OF SEQ ID NOS: 48

<210> SEQ ID NO 1
<211> LENGTH: 1619
<212> TYPE: DNA
<213> ORGANISM: Homo sapiens
<220> FEATURE:
<221> NAME/KEY: CDS
<222> LOCATION: (50)..(478)

<400> SEQUENCE: 1
ccgccagatt tgaatcgcgg gacccgttgg cagaggtggc ggcggcggc atg ggt        55
                                                    Met Gly
                                                      1 gcc ccg acg ttg ccc cct gcc tgg cag ccc ttt ctc aag gac cac cgc    103
Ala Pro Thr Leu Pro Pro Ala Trp Gln Pro Phe Leu Lys Asp His Arg
          5                  10                 15 atc tct aca ttc aag aac tgg ccc ttc ttg gag ggc tgc gcc tgc acc    151
Ile Ser Thr Phe Lys Asn Trp Pro Phe Leu Glu Gly Cys Ala Cys Thr
         20                 25                 30 ccg gag cgg atg gcc gag gct ggc ttc atc cac tgc ccc act gag aac    199
Pro Glu Arg Met Ala Glu Ala Gly Phe Ile His Cys Pro Thr Glu Asn
     35                 40                 45                 50 gag cca gac ttg gcc cag tgt ttc ttc tgc ttc aag gag ctg gaa ggc    247
Glu Pro Asp Leu Ala Gln Cys Phe Phe Cys Phe Lys Glu Leu Glu Gly
                 55                 60                 65 tgg gag cca gat gac gac ccc ata gag gaa cat aaa aag cat tcg tcc    295
Trp Glu Pro Asp Asp Asp Pro Ile Glu Glu His Lys Lys His Ser Ser
             70                 75                 80 ggt tgc gct ttc ctt tct gtc aag aag cag ttt gaa gaa tta acc ctt    343
Gly Cys Ala Phe Leu Ser Val Lys Lys Gln Phe Glu Glu Leu Thr Leu
         85                 90                 95 ggt gaa ttt ttg aaa ctg gac aga gaa aga gcc aag aac aaa att gca    391
Gly Glu Phe Leu Lys Leu Asp Arg Glu Arg Ala Lys Asn Lys Ile Ala
    100                105                110 aag gaa acc aac aat aag aag aaa gaa ttt gag gaa act gcg aag aaa    439
Lys Glu Thr Asn Asn Lys Lys Lys Glu Phe Glu Glu Thr Ala Lys Lys
115                120                125                130 gtg cgc cgt gcc atc gag cag ctg gct gcc atg gat tga ggcctctggc    488
Val Arg Arg Ala Ile Glu Gln Leu Ala Ala Met Asp
                135                140 cggagctgcc tggtcccaga gtggctgcac cacttccagg gtttattccc tggtgccacc   548
agccttcctg tgggcccctt agcaatgtct taggaaagga gatcaacatt ttcaaattag   608
atgtttcaac tgtgctcctg ttttgtcttg aaagtggcac cagaggtgct tctgcctgtg   668
cagcgggtgc tgctggtaac agtggctgct tctctctctc tctctctttt ttgggggctc   728 attttttgctg ttttgattcc cgggcttacc aggtgagaag tgagggagga agaaggcagt   788
gtcccttttg ctagagctga cagctttgtt cgcgtgggca gagccttcca cagtgaatgt   848
gtctggacct catgttgttg aggctgtcac agtcctgagt gtggacttgg caggtgcctg   908
```

```
ttgaatctga gctgcaggtt ccttatctgt cacacctgtg cctcctcaga ggacagtttt      968
tttgttgttg tgttttttg ttttttttt ttggtagatg catgacttgt gtgtgatgag       1028
agaatggaga cagagtccct ggctcctcta ctgtttaaca acatggcttt cttattttgt      1088
ttgaattgtt aattcacaga atagcacaaa ctacaattaa aactaagcac aaagccattc      1148
taagtcattg gggaaacggg gtgaacttca ggtggatgag gagacagaat agagtgatag      1208
gaagcgtctg gcagatactc cttttgccac tgctgtgtga ttagacaggc ccagtgagcc      1268
gcggggcaca tgctggccgc tcctccctca gaaaaaggca gtggcctaaa tcctttttaa      1328
atgacttggc tcgatgctgt gggggactgg ctgggctgct gcaggccgtg tgtctgtcag      1388
cccaaccttc acatctgtca cgttctccac acgggggaga gacgcagtcc gcccaggtcc      1448
ccgctttctt tggaggcagc agctcccgca gggctgaagt ctggcgtaag atgatggatt      1508
tgattcgccc tcctccctgt catagagctg cagggtggat tgttacagct tcgctggaaa      1568
cctctggagg tcatctcggc tgttcctgag aaataaaaag cctgtcattt c               1619
```

<210> SEQ ID NO 2
<211> LENGTH: 21
<212> TYPE: DNA
<213> ORGANISM: Artificial Sequence
<220> FEATURE:
<223> OTHER INFORMATION: PCR Primer

<400> SEQUENCE: 2
aaggaccacc gcatctctac a                                                 21

<210> SEQ ID NO 3
<211> LENGTH: 22
<212> TYPE: DNA
<213> ORGANISM: Artificial Sequence
<220> FEATURE:
<223> OTHER INFORMATION: PCR Primer

<400> SEQUENCE: 3
ccaagtctgg ctcgttctca gt                                                22

<210> SEQ ID NO 4
<211> LENGTH: 23
<212> TYPE: DNA
<213> ORGANISM: Artificial Sequence
<220> FEATURE:
<223> OTHER INFORMATION: PCR Probe

<400> SEQUENCE: 4
cgaggctggc ttcatccact gcc                                               23

<210> SEQ ID NO 5
<211> LENGTH: 19
<212> TYPE: DNA
<213> ORGANISM: Artificial Sequence
<220> FEATURE:
<223> OTHER INFORMATION: PCR Primer

<400> SEQUENCE: 5
gaaggtgaag gtcggagtc                                                    19

<210> SEQ ID NO 6
<211> LENGTH: 20
<212> TYPE: DNA
<213> ORGANISM: Artificial Sequence
<220> FEATURE:

```
<223> OTHER INFORMATION: PCR Primer

<400> SEQUENCE: 6
gaagatggtg atgggatttc                                               20

<210> SEQ ID NO 7
<211> LENGTH: 20
<212> TYPE: DNA
<213> ORGANISM: Artificial Sequence
<220> FEATURE:
<223> OTHER INFORMATION: PCR Probe

<400> SEQUENCE: 7
caagcttccc gttctcagcc                                               20

<210> SEQ ID NO 8
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 8
gcgattcaaa tctggcgg                                                 18

<210> SEQ ID NO 9
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 9
cctctgccaa cgggtccc                                                 18

<210> SEQ ID NO 10
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 10
tgagaaaggg ctgccagg                                                 18

<210> SEQ ID NO 11
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 11
ttcttgaatg tagagatg                                                 18

<210> SEQ ID NO 12
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 12
ggcgcagccc tccaagaa                                                 18
```

```
<210> SEQ ID NO 13
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 13
caagtctggc tcgttctc                                                        18

<210> SEQ ID NO 14
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 14
tccagctcct tgaagcag                                                        18

<210> SEQ ID NO 15
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 15
ggtcgtcatc tggctccc                                                        18

<210> SEQ ID NO 16
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 16
gcttcttgac agaaagga                                                        18

<210> SEQ ID NO 17
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 17
ggttaattct tcaaactg                                                        18

<210> SEQ ID NO 18
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 18
tcttggctct ttctctgt                                                        18

<210> SEQ ID NO 19
<211> LENGTH: 18
<212> TYPE: DNA
<213> ORGANISM: Artificial Sequence
<220> FEATURE:
<223> OTHER INFORMATION: Antisense Oligonucleotide
```

-continued

<400> SEQUENCE: 19
tcttattgtt ggtttcct                                                        18

<210> SEQ ID NO 20
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 20
tcgcagtttc ctcaaatt                                                        18

<210> SEQ ID NO 21
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 21
cgatggcacg gcgcactt                                                        18

<210> SEQ ID NO 22
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 22
cctggaagtg gtgcagcc                                                        18

<210> SEQ ID NO 23
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 23
acaggaaggc tggtggca                                                        18

<210> SEQ ID NO 24
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 24
tttgaaaatg ttgatctc                                                        18

<210> SEQ ID NO 25
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 25
acagttgaaa catctaat                                                        18

<210> SEQ ID NO 26
<211> LENGTH: 18

```
<212> TYPE: DNA
<213> ORGANISM: Artificial Sequence
<220> FEATURE:
<223> OTHER INFORMATION: Antisense Oligonucleotide

<400> SEQUENCE: 26
ctttcaagac aaaacagg                                                   18

<210> SEQ ID NO 27
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 27
acaggcagaa gcacctct                                                   18

<210> SEQ ID NO 28
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 28
aagcagccac tgttacca                                                   18

<210> SEQ ID NO 29
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 29
aaagagagag agagagag                                                   18

<210> SEQ ID NO 30
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 30
tccctcactt ctcacctg                                                   18

<210> SEQ ID NO 31
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 31
agggacactg ccttcttc                                                   18

<210> SEQ ID NO 32
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 32
```

-continued ccacgcgaac aaagctgt                                                18

<210> SEQ ID NO 33
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 33
actgtggaag gctctgcc                                                18

<210> SEQ ID NO 34
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 34
aggactgtga cagcctca                                                18

<210> SEQ ID NO 35
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 35
tcagattcaa caggcacc                                                18

<210> SEQ ID NO 36
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 36
attctctcat cacacaca                                                18

<210> SEQ ID NO 37
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 37
tgttgttaaa cagtagag                                                18

<210> SEQ ID NO 38
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 38
tgtgctattc tgtgaatt                                                18

<210> SEQ ID NO 39
<211> LENGTH: 18
<212> TYPE: DNA
<213> ORGANISM: Artificial Sequence

```
<220> FEATURE:
<223> OTHER INFORMATION: Antisense Oligonucleotide

<400> SEQUENCE: 39
gacttagaat ggctttgt                                                 18

<210> SEQ ID NO 40
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 40
ctgtctcctc atccacct                                                 18

<210> SEQ ID NO 41
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 41
aaaaggagta tctgccag                                                 18

<210> SEQ ID NO 42
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 42
gaggagcggc cagcatgt                                                 18

<210> SEQ ID NO 43
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 43
ggctgacaga cacacggc                                                 18

<210> SEQ ID NO 44
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 44
ccgtgtggag aacgtgac                                                 18

<210> SEQ ID NO 45
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 45
tacgccagac ttcagccc                                                 18
```

```
<210> SEQ ID NO 46
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 46
atgacaggga ggagggcg                                                 18

<210> SEQ ID NO 47
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 47
gccgagatga cctccaga                                                 18

<210> SEQ ID NO 48
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 48
taagctgttc tatgtgtt                                                 18
```